United States Patent
Deinlein et al.

(10) Patent No.: US 10,111,642 B2
(45) Date of Patent: Oct. 30, 2018

(54) POSITIONING OF A MOBILE X-RAY DETECTOR

(71) Applicant: SIEMENS HEALTHCARE GMBH, Erlangen (DE)

(72) Inventors: Andreas Deinlein, Bayreuth (DE); Thomas Dippl, Pressath (DE); Susanne Dornberger, Erlangen (DE); Michael Fuhrmann, Herzogenaurach (DE); Sultan Haider, Erlangen (DE); Ralf Nanke, Neunkurchen am Brand (DE)

(73) Assignee: Siemens Healthcare GmbH, Erlangen (DE)

( * ) Notice: Subject to any disclaimer, the term of this patent is extended or adjusted under 35 U.S.C. 154(b) by 203 days.

(21) Appl. No.: 15/183,993

(22) Filed: Jun. 16, 2016

(65) Prior Publication Data
US 2017/0360394 A1 Dec. 21, 2017
US 2018/0220989 A9 Aug. 9, 2018

(30) Foreign Application Priority Data
Jun. 16, 2015 (DE) .................... 10 2015 211 057

(51) Int. Cl.
*A61B 6/00* (2006.01)
(52) U.S. Cl.
CPC ............ *A61B 6/587* (2013.01); *A61B 6/4405* (2013.01); *A61B 6/4464* (2013.01)
(58) Field of Classification Search
None
See application file for complete search history.

(56) References Cited

U.S. PATENT DOCUMENTS

| 7,643,615 B2 | 1/2010 | Wang et al. |
| 8,690,426 B2 | 4/2014 | Liu et al. |
| 2006/0109958 A1 | 5/2006 | Ertel et al. |
| 2006/0261296 A1 | 11/2006 | Heath et al. |
| 2008/0159486 A1* | 7/2008 | Hesl ............ A61B 6/4233 378/189 |
| 2012/0039447 A1* | 2/2012 | Lalena ............ A61B 6/08 378/206 |

FOREIGN PATENT DOCUMENTS

| DE | 102011051053 A1 | 12/2011 |
| DE | 102013219137 A1 | 3/2015 |
| DE | 102013221383 A1 | 4/2015 |
| DE | 102014210897 A1 | 12/2015 |
| WO | 2015185235 A1 | 12/2015 |

\* cited by examiner

*Primary Examiner* — Hoon Song
(74) *Attorney, Agent, or Firm* — Laurence Greenberg; Werner Stemer; Ralph Locher

(57) ABSTRACT

A positioning device for a mobile x-ray detector, an x-ray device containing such a mobile positioning device, and a method mutually align a mobile x-ray detector and an x-ray emitter in relation to one another. In order to enable exact mutual alignment or positioning of the mobile x-ray detector in relation to the x-ray emitter, a positioning device is used for a mobile x-ray detector. The positioning device contains at least one marker and/or at least one sensor for determining the position and/or the orientation of the positioning device and contains a number of connection elements for establishing a mechanical connection between the positioning device and the mobile x-ray detector.

9 Claims, 3 Drawing Sheets

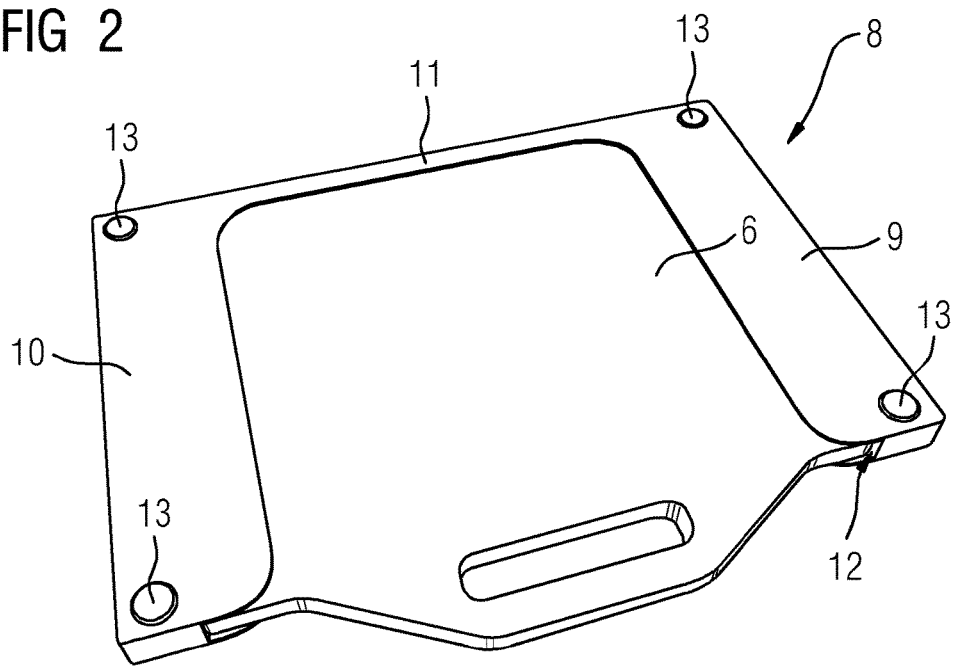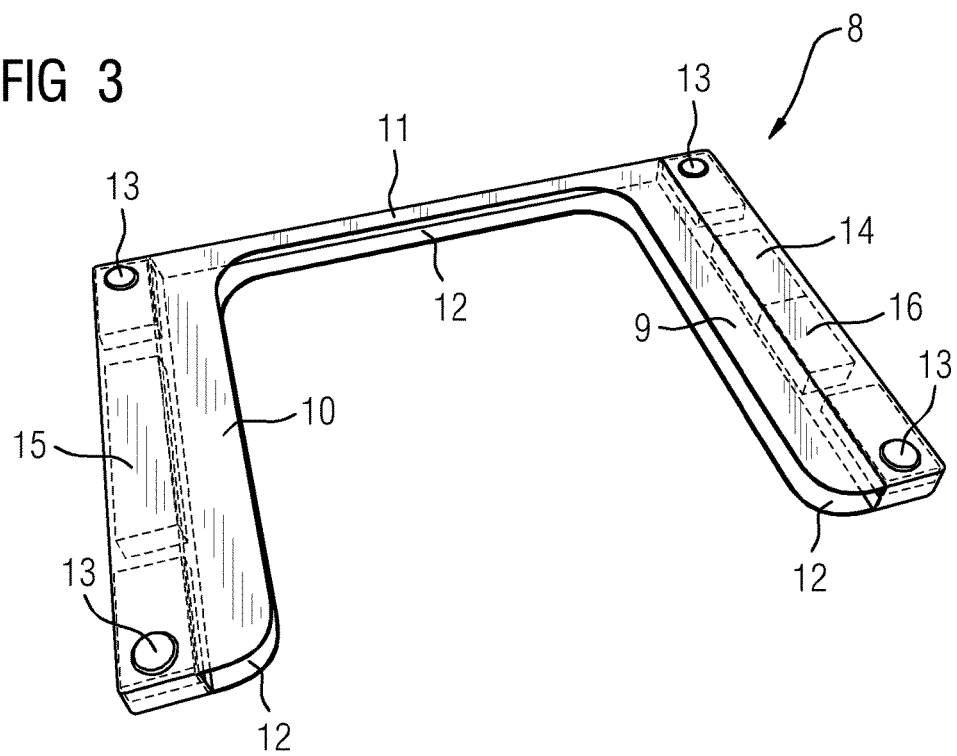

POSITIONING OF A MOBILE X-RAY DETECTOR

CROSS-REFERENCE TO RELATED APPLICATION

This application claims the priority, under 35 U.S.C. § 119, of German application DE 10 2015 211 057.5, filed Jun. 16, 2015; the prior application is herewith incorporated by reference in its entirety.

BACKGROUND OF THE INVENTION

Field of the Invention

The invention relates to a positioning device for a mobile x-ray detector, an x-ray device containing such a positioning device and a method for mutually aligning a mobile x-ray detector and an x-ray emitter in relation to one another.

In order to record an image of a patient in an x-ray device, it is necessary for an x-ray emitter to be aligned in such a way that the x-rays emitted thereby are incident on an x-ray detector through the patient such that the x-rays are registered by the x-ray detector and able to be processed further to form an image of the patient.

It is sufficient to carry out the alignment once in an x-ray device in which the x-ray detector and the x-ray emitter are securely installed and arranged at a fixed position relative to one another, for example because there is mechanical coupling between x-ray emitter and x-ray detector. Apart from occasional testing and servicing, the alignment between these parts remains unchanged.

However, there are a series of x-ray devices which have various degrees of freedom in respect of the positioning of the x-ray emitter and/or x-ray detector in order thereby to enable different types of examinations and adaptations to the anatomy of the respective patient. Especially if the x-ray emitter and x-ray detector can be moved independently of one another, i.e. if they are not rigidly connected to one another as in the case of e.g. a C-arm or a computed tomography scanner, the ideal positioning of these two components for the respective examination is a complicated problem. Here, requirements in terms of efficiency should be taken into account, i.e. the positioning of the emitter and detector should be carried out as quickly as possible in order to enable an efficient workflow.

This is particularly demanding when use is made of mobile x-ray detectors. By way of example, such a mobile detector can be connected only by way of a flexible cable with the x-ray device, with the cable ensuring the energy supply of the device and the data transfer. However, a mobile x-ray detector can alternatively also contain an autonomous power supply, for example by way of batteries or accumulators, and have a wireless data connection for transmitting the received signals, for example by way of radio waves, other electromagnetic couplings or else by infrared.

The particular advantage of these mobile x-ray detectors, in particular of those with a wireless data connection, is that they can be used in a particularly flexible manner. Thus, for example, it is possible to prepare a patient for a recording by virtue of already placing the patient onto a movable patient couch with a mobile x-ray detector prior to the examination. The patient can then be pushed under the x-ray emitter within a short period of time for the purposes of the recording.

In the case of such mobile x-ray detectors with a variable pose, it is necessary prior to carrying out an image recording to bring the x-ray detectors into a fixed and defined position relative to the x-ray emitter in order to enable a predetermined image recording of the patient. In the case of mobile x-ray detectors, the practice of directly and immediately determining the spatial pose (position and orientation) of the x-ray detector by appropriate position sensors so that the x-ray emitter can be aligned appropriately is known. By way of example, such x-ray detectors are described in U.S. patent publication No. 2006/0109958A1 and published, non-prosecuted German patent application DE 10 2011 051 053 A1.

However, such a procedure is relatively complicated from a measurement point of view, since an immediate optical determination of the pose of the x-ray detector is not always possible from the x-ray emitter as the x-ray detector, on account of the function thereof, must often be arranged behind the patient or the object through which radiation should pass. Moreover, it is difficult to arrange the measuring device in the interior of the detector housing due to the generally very restricted available free housing volume.

SUMMARY OF THE INVENTION

It is an object of the present invention to enable an exact mutual alignment or the positioning of the mobile x-ray detector in relation to the x-ray emitter. This object is achieved by a positioning device, by an x-ray device and by a method. Advantageous embodiments of the invention are specified in the dependent claims.

The advantages and refinements explained below in conjunction with the positioning device also apply analogously to the x-ray device according to the invention and to the method according to the invention, and vice versa.

The positioning device according to the invention for a mobile x-ray detector contains at least one marker and/or at least one sensor for determining the position of the positioning device and a number of connection elements for establishing a mechanical connection between the positioning device and the mobile x-ray detector. In a preferred embodiment of the invention, the position and/or the orientation of the x-ray detector is registered with the aid of a measuring device.

The x-ray device according to the invention contains an x-ray emitter, a mobile x-ray detector and a positioning device according to the invention which is connectable to the mobile x-ray detector.

The method according to the invention for mutually aligning a mobile x-ray detector and an x-ray emitter in relation to one another contains connecting the mobile x-ray detector to a positioning device with the aid of a number of connection elements of the positioning device, determining the position of the mobile x-ray detector and providing the position data with the aid of the positioning device and also automatically aligning the x-ray emitter in relation to the mobile x-ray detector, and/or vice versa, using the position data provided. In a preferred embodiment of the invention, the position and/or the orientation of the x-ray detector is determined, the position and/or orientation data are provided with the aid of the positioning device and the automatic alignment of the x-ray emitter in relation to the mobile x-ray detector, and/or vice versa, is carried out using the position and/or orientation data provided.

It is a core concept of the invention no longer to provide the measuring device for determining the position and/or the orientation of the x-ray detector directly in the x-ray detector itself, i.e. generally in the interior of the detector housing. Instead, these measuring devices are provided as part of a positioning device which is manageable independently of the x-ray detector but optionally connectable to the x-ray detector. The pose of the x-ray detector is no longer detected immediately. Rather, the position and/or orientation of the positioning device connected to the x-ray detector in a defined manner is established and the pose of the x-ray detector is determined therefrom.

This allows an exact mutual alignment or positioning of the mobile x-ray detector in relation to the x-ray emitter to be obtained, without it being necessary to undertake changes on the x-ray detector itself. In particular, no structural changes of the x-ray detector, such as reconstructions in the interior of the detector housing, are required. The function of the x-ray detector also remains completely unchanged. Hence, standardized x-ray detectors can be used for the x-ray device according to the invention without needing to dispense with exact positioning.

The positioning device and, therewith, the mobile x-ray detector are positioned in space, i.e. usually placed below the patient. By way of the positioning device, the measuring devices (markers and/or sensors) are associated in a spatially secured manner with the x-ray detector and co-moved therewith. The exact spatial pose of the x-ray detector relative to the positioning device is known in the assembled state, i.e. when a connection is established between the positioning device and x-ray detector, due to the exactly defined, detachable and, in the process, precisely repeatable connection between the positioning device and the mobile x-ray detector. Therefore, by registering or establishing the position and/or the orientation of the positioning device, it is also possible to register or establish the position and/or the orientation of the mobile x-ray detector and hence the relative pose thereof in relation to the x-ray emitter.

Once a relative position or the orientation of the x-ray detector is known, it is possible to align the x-ray emitter onto the x-ray detector, possibly in an automatic manner. Expressed differently, it is possible to compare an actual position of the x-ray emitter with an intended position thereof, as a result of which a correction in the position of the x-ray emitter is made possible. Thus, the x-ray emitter can advantageously be brought into a desired position relative to the x-ray detector.

Alternatively, the known position and/or orientation of the x-ray detector also permits a comparison of an actual position of the x-ray detector with an intended position thereof, as a result of which a correction in the position of the positioning device, and hence of the x-ray detector arranged thereon, is made possible. Thus, the x-ray detector can advantageously be brought into a desired position relative to the x-ray emitter.

The x-ray device according to the invention, which, in addition to the preferably variably positionable x-ray emitter and the mobile x-ray detector for recording an x-ray projection of an examination object arranged on an examination table, also contains the positioning device according to the invention, additionally has a positioning aid connectable to the x-ray emitter or to a ceiling mount of the x-ray device in a preferred embodiment of the invention. Here, the positioning aid is arranged in a known, defined relative pose in relation to the x-ray emitter.

Similar to the positioning device, this positioning aid contains at least one marker and/or at least one sensor for establishing the position and/or the orientation of the positioning device for the mobile x-ray detector and a number of connection elements for establishing a mechanical connection between the positioning aid and the x-ray emitter or the ceiling mount. In the assembled state, it serves together with the positioning device to register or determine the position and/or the orientation of the x-ray detector.

The markers and/or sensors of the positioning device or of the positioning aid are designed to register or establish a relative position between the x-ray detector and the x-ray emitter. In the process, they can comprise any suitable position and/or orientation encoders which permit a unique position and/or orientation determination.

If the measuring devices are situated in the region of the free line of sight of the x-ray emitter, i.e. if they are visible and not covered by a patient during an image acquisition of the patient using the x-ray detector, the position and/or the orientation of the x-ray detector can be established very easily by optical means, for example by attaching optical markers. By way of example, the markers are a number of optically registrable position markers, which are attached at the positioning device in such a way that a registration of the position of the position marks renders a spatial determination of the positioning device possible. In this case, the positioning aid preferably contains an optical acquisition system such as e.g. a camera, which determines the spatial pose of the positioning device, and hence of the x-ray detector. The signal from the camera can be automatically registered and processed by a control device such that it is advantageously possible to provide an x-ray device which independently poses the patient and/or carries out an automatic alignment of the x-ray emitter. In one possible embodiment, the positioning aid contains two cameras. A second camera advantageously enables a view of regions which are covered up for the first camera, for example by a patient. Moreover, a second camera enables stereoscopic registration, and so the pose of a position mark is registrable not only in two dimensions but also three-dimensionally in space. As a result, fewer pose marks may suffice for registering the position and/or the orientation of the x-ray detector. In one possible embodiment, the positioning aid contains one or more 3D or depth cameras instead.

In one conceivable embodiment, the positioning aid contains a light source for emitting a light beam. Then, positioning can advantageously be carried out by operating staff without further aids by virtue of the light beam being aligned with a position mark. A manual alignment can also be assisted by appropriate optical signals, for example by the emission of a central connecting line between the x-ray emitter and the center of the x-ray detector and by displaying the central beam in the beam cone or by optically shown boundaries of the beam cone.

Another possibility for determining the position and/or orientation of the positioning device and hence of the x-ray detector in the case of a free line of sight lies in the use of ultrasonic transmitters and receivers.

However, position and/or orientation of the x-ray detector can also be determined on an electromagnetic basis such that no free line of sight is necessary. Advantageously, magnetic coils or other position markers registrable by electromagnetic signals in the radiofrequency range can be used as electromagnetic position and orientation encoders, in particular radio frequency identification device (RFID) transponders. In this case, appropriate RFID reading devices are attached in the positioning aid. Radio waves pass through the patient but are harmless at the same time. Therefore, it is possible that the position marks are also covered by the patient and nevertheless registered, simplifying handling. In particular, care need not be taken especially to ensure that the position marks remain visible during the preparation of the patient.

The positioning device and/or the positioning aid contains a number of suitable transmitters and/or receivers, and also sensors and/or detectors for determining the position and/or orientation of the positioning device. Here, the positioning device and/or the positioning aid can also, for example, have a distance measuring device and/or a compass and/or a gyroscope and/or an accelerometer and/or a pose sensor, e.g. an angle encoder relative to the gravitational field, wherein these further measuring devices can be used additionally for determining the position and/or orientation of the x-ray detector.

In a simple refinement of the invention, the positioning device only has markers, e.g. optical or electromagnetic markers, and the positioning aid only has sensors, e.g. cameras or RFID readers. However, preferably both the positioning device and the positioning aid contains both a number of markers and a number of sensors. Here, the markers on the positioning device interact with the sensors on the positioning aid and the sensors on the positioning device interact with the markers on the positioning aid. It is advantageous if the measurement procedures of the available marker-sensor pairs are monitored such that only those measurement results originating from suitable marker-sensor pairs are used for establishing the position and/or orientation of the x-ray detector, while unsuitable measuring device, for example those which do not supply any or any usable measurement results, for example because there is no optical line of sight between marker and sensor due to the position of the patient, remain unconsidered.

Preferably, the positioning device has a computer unit such that the calculation of the position and/or orientation of the x-ray detector can be carried out in the positioning device itself. Here, in one embodiment of the invention, the position and/or the orientation of the mobile x-ray detector is determined with the aid of the computer unit on the basis of the measurement data obtained by the measuring device. Here, this can be the relative position and/or orientation of the x-ray detector in relation to the x-ray emitter, or else an absolute determination of the pose in space.

The computer unit preferably contains a computer program stored in storage of the computer unit, which computer program is executed during operation and, in the process, carries out calculations for determining the position and/or orientation of the x-ray detector. This established position and/or orientation of the x-ray detector can then be output or stored or processed further for further use.

The computer unit is preferably embodied as part of the positioning device. However, the computer unit can also be part of the positioning aid or else it can be a functional unit embodied independently of the positioning device and the positioning aid and arranged at a distance therefrom.

In a further conceivable embodiment, the positioning device and/or the positioning aid furthermore has an interface, by which interface the position and/or orientation or pose of the x-ray detector, which is detected or established with the aid of the computer unit, is provided.

In order to provide the established position and/or orientation data, the interface of the positioning device or of the positioning aid is connected or at least intermittently connectable to the computer unit. The position and/or orientation data are preferably provided to a control unit of the x-ray device by virtue of being transmitted, preferably in a wireless manner, to the latter. The interface contains correspondingly suitable provision or transmission device, in particular a transmitter which preferably transmits data wirelessly. There preferably is wireless infrared communication or the data transmission is carried out by way of a Bluetooth interface or using different near field communication technology.

Alternatively, it is also possible that only the data necessary for determining position and/or orientation of the x-ray detector is sent directly to the control unit of the x-ray device, where the data is processed accordingly.

Subsequently, there is a preferably automatic alignment of the x-ray emitter in relation to the mobile x-ray detector using the position and/or orientation data provided. To this end, the x-ray device has a control and computer unit serving as a device for positioning the x-ray emitter in one conceivable embodiment of the invention, the control and computer unit aligning the x-ray emitter with the x-ray detector after it previously, where necessary, carries out the calculations required in this respect.

The positioning device and/or the positioning aid have a power supply for supplying the measuring device(s), the computer unit and/or the interface with power. Here, this is preferably an autonomous power supply in the form of a rechargeable battery. It is particularly advantageous if the positioning device or the positioning aid is designed in such a way that recharging of the battery can be carried out wirelessly. In one conceivable embodiment, the positioning device has an electrical connection to the x-ray detector, by which both the power supply and the data transmission take place.

In a further advantageous embodiment, the positioning device has an arm which is movable from a first position to a second position and back again, at the free end of which arm at least one marker and/or sensor is arranged, wherein this at least one marker and/or sensor has a greater distance from the mobile x-ray detector in the second position of the arm than in the first position of the arm. If the marker or sensor attached to the free end of the arm is a measuring device which requires a free line of sight to a counter piece of the marker-sensor pair attached at the positioning aid and if this free line of sight is not given in the first position of the arm, then the required free line of sight can be established by moving the arm into the second position. Preferably, the arm has a length which ensures that the free end of the arm is no longer covered by the patient in the direction of the positioning aid in the second position in the case of a typical arrangement of the positioning device under a patient placed onto an examination table.

In one embodiment of the invention, the movable arm is embodied as a swivelable or extendable, e.g. telescopable, arm. Preferably, the positioning device has an arm which is fastened to a main body of the positioning device with the aid of a swivel joint and which is swivelable from an initial position into a swiveled position.

A number of connection elements of the positioning device serve to connect the mobile x-ray detector to the positioning device. Here, the connection elements of the positioning device are preferably designed in such a way that they fix the x-ray detector in a predetermined relative position with respect to the positioning device. The connection elements of the positioning aid are likewise designed to fix the positioning aid in a predetermined relative position at the x-ray emitter or at the ceiling mount. In both cases, connection elements which are embodied for establishing a latching and/or snap-in connection between the positioning device and the mobile x-ray detector were found to be particularly advantageous. Such connection elements render it possible in a simple and cost-effective manner to set the relative position between positioning device and x-ray detector or between positioning aid and x-ray detector or ceiling mount in an exact and permanent manner.

In one conceivable embodiment, the positioning device is embodied as a frame for accommodating and/or holding the mobile x-ray detector. The embodiment as a frame preferably provides for a substantially U-shaped structure to engage around the x-ray detector, wherein the measuring device, the computer unit and/or the interface are arranged in one or both U-limbs and/or in the U-base. Here, the frame preferably forms a slot for the mobile x-ray detector, particularly if the x-ray detector is a flat-panel detector. The frame then has an accommodation groove suitable for accommodating the x-ray detector, at least at the U-limbs thereof.

The components provided in the positioning device or in the positioning aid, such as measuring device, battery, etc., can be arranged in the interior of the respective main body. However, the main bodies of positioning device and positioning aid can also be embodied in such a way that they comprise corresponding receptacles for these components. The components can then be inserted into the main body according to requirements.

In a further conceivable embodiment of the invention, the positioning device is embodied as a closed frame which surrounds the x-ray detector on all sides. Preferably, the x-ray detector is connected to this type of frame by forming a latching or snap-in connection.

In a further conceivable embodiment of the invention, the positioning device is embodied as a type of case, in the interior of which the mobile x-ray detector can be accommodated. Compared to an embodiment as a U-shaped holding frame, the case variant is distinguished by virtue of the x-ray detector being held between a base element and a lid element.

An embodiment of the invention in which the positioning device and/or the positioning aid is produced by an additive manufacturing process was found to be particularly advantageous. These are processes, known from the prior art, for producing any type of three-dimensional object, usually by selective solidification of a construction material such as a plastic, metal or ceramic applied layer-by-layer. In addition to stereolithography, examples of such layered construction processes are laser sintering or selective mask sintering. With the aid of such an additive manufacturing process, the positioning devices and/or positioning aids used in the context of the present invention, preferably including the measuring device and the power supply, can be manufactured in a simple manner, quickly and cost-effectively and individually adapted to the respective application.

Therefore, the invention provides a system for automatic alignment of the x-ray emitter, applicable in a particularly advantageous manner in the case of wireless x-ray detectors. Here, the type of the x-ray device plays a secondary role. However, the invention can be employed particularly advantageously in the case of radiographic x-ray devices. The modular design and the variability of this system enable universal applicability. Depending on the wish of the user, the positioning device and the positioning aid can be provided with selected measuring devices. Since modifications need not be undertaken on either the x-ray detector itself or on the x-ray emitter, the positioning device and the positioning aid can be integrated in a particularly simple manner in the available x-ray device. The positioning aid can be provided at the x-ray emitter and/or at a ceiling mount.

Other features which are considered as characteristic for the invention are set forth in the appended claims.

Although the invention is illustrated and described herein as embodied in positioning of a mobile x-ray detector, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 2 is a diagrammatic, perspective view of a mobile x-ray detector with a first positioning device;

FIG. 3 is a perspective view showing the first positioning device from FIG. 2;

DETAILED DESCRIPTION OF THE INVENTION

Figure 1:
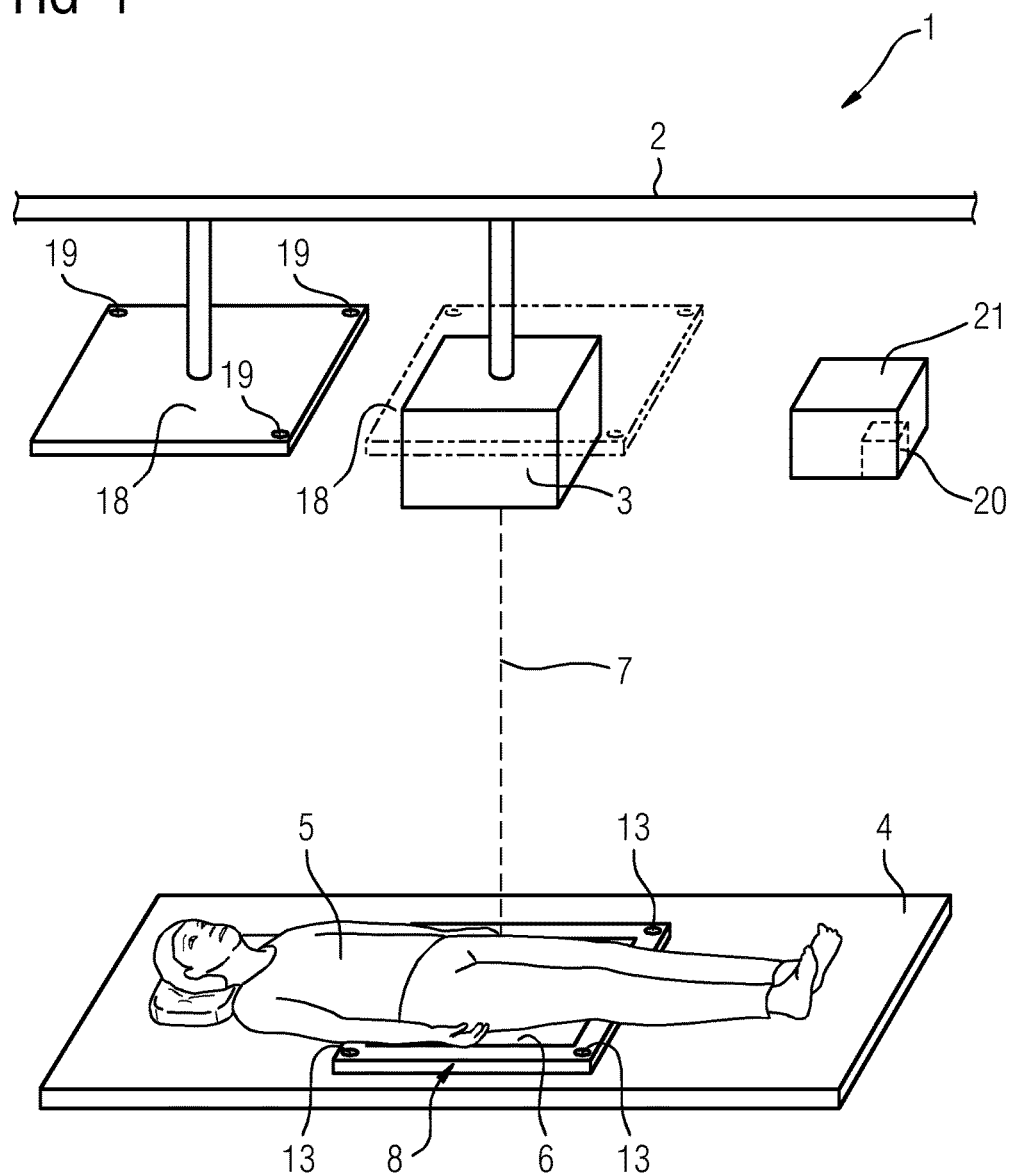
FIG. 1 is a diagrammatic, perspective view of an x-ray device.

In the figures, the same reference signs correspond to elements with an equivalent or comparable function. Referring now to the figures of the drawings in detail and first, particularly to FIG. 1 thereof, there is shown a radiographic x-ray device 1. The x-ray device 1 has an x-ray tube 3 as an x-ray emitter which is displaceable on a ceiling mount 2. A patient 5 as an examination object is situated on a patient couch 4 which serves as an examination table. A wireless mobile x-ray detector configured as a flat-panel detector 6 is provided under the patient 5. The x-ray tube 3 is positioned relative to the flat-panel detector 6 in such a way that these can interact for recording the patient 5. A central beam 7 pointing from the x-ray tube 3 into the center of the flat-panel detector 6 has been drawn.

The flat-panel detector 6 is connected to a positioning device 8 which is embodied in the style of a U-shaped frame. The positioning device 8 has a continuous accommodation groove 12, which extends over two U-shaped limbs 9, 10 and a U-base 11 and into which the flat-panel detector 6 can be inserted, as shown in FIG. 2.

As illustrated in FIG. 3, in which it is depicted in a transparent manner, the positioning device 8 contains respectively one ultrasonic transmitter 13 as a marker in the four corners thereof. Moreover, a microcontroller 14 serving as a computer unit and a battery 15 are provided in the U-limbs 9, 10.

Moreover, the x-ray device 1 contains a positioning aid 18, which is connected to the ceiling mount 2 and arranged at a distance from the x-ray tube 3. Alternatively, this positioning aid 18 can also be fastened directly to the x-ray tube 3, as indicated in FIG. 1 by broken lines. The positioning aid 18 can likewise be embodied as a type of frame or else it can be available in any other suitable form. It contains one or more suitable ultrasonic receivers 19 as a sensor for forming marker-sensor pairs with the ultrasonic transmitters 13 in the positioning device 8.

The ultrasonic transmitters and receivers 13, 19 serve as measuring devices to establish the position and/or the orientation of the positioning device 8 and hence to establish the position and/or the orientation of the flat-panel detector 6 arranged in a defined manner in relation to the positioning device 8.

Instead of the ultrasonic transmitter and receiver 13, 19, or in addition thereto, the positioning device 8 and the positioning aid 18 can also have different markers and sensors.

In the exemplary embodiment described here, the relative position of the flat-panel detector 6 in relation to the x-ray tube 3 is determined. In addition to determining the relative position, the orientation of the flat-panel detector 6 may also be determined, preferably in relation to an axis of symmetry of the x-ray tube 3. All calculations required in this respect are carried out in the microcontroller 14 which, to this end, executes suitable software.

An infrared transmitter 16, which is connected to the microcontroller 14 and is likewise part of the positioning device 8, serves as an interface for providing the established position and/or orientation data to a control unit 21 of the x-ray device 1 equipped with an infrared receiver 20. The control unit 21, which is merely indicated schematically in FIG. 1, controls the subsequent automatic alignment of the x-ray tube 3 in relation to the flat-panel detector 6, which is already situated in the recording position, by using the provided position and/or orientation data and, to this end, it is connected to a motor-driven displacement unit (not depicted here) for the x-ray tube 3. Alternatively or additionally, the flat-panel detector 6 is aligned, for example by way of the motor-driven drive of the patient couch 4.

Figure 4:
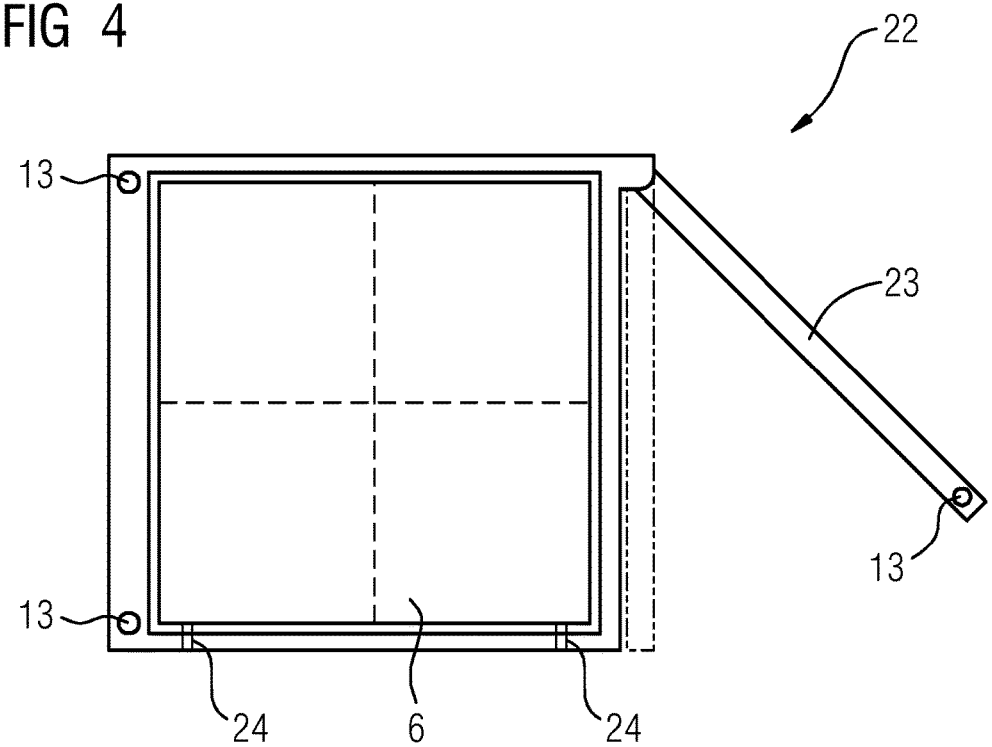
FIG. 4 is a front view of a second positioning device.

In the exemplary embodiment depicted in FIG. 4, a positioning device 22 has an arm 23, which can be moved from an initial position, indicated by broken lines, into a swiveled position and back again, with one of the ultrasonic transmitters 13 being arranged at the free end of said arm. In the swivel position, the ultrasonic transmitter 13 is at a greater distance from the flat-panel detector 6 accommodated in the positioning device 22 than in the initial position of the arm 23, and so it protrudes laterally next to the patient 5 and there is a free line of sight in the direction of the ultrasonic receiver 19 on the positioning aid 18. In contrast to the U-shaped frame type, the positioning device 22 shown here has a circumferential, closed frame, which encloses the flat-panel detector 6 on all sides. Latching elements 24 provided at the positioning device 22 for establishing a latching connection between the flat-panel detector 6 and the positioning device 22 are only indicated symbolically in FIG. 4.

Figure 5:
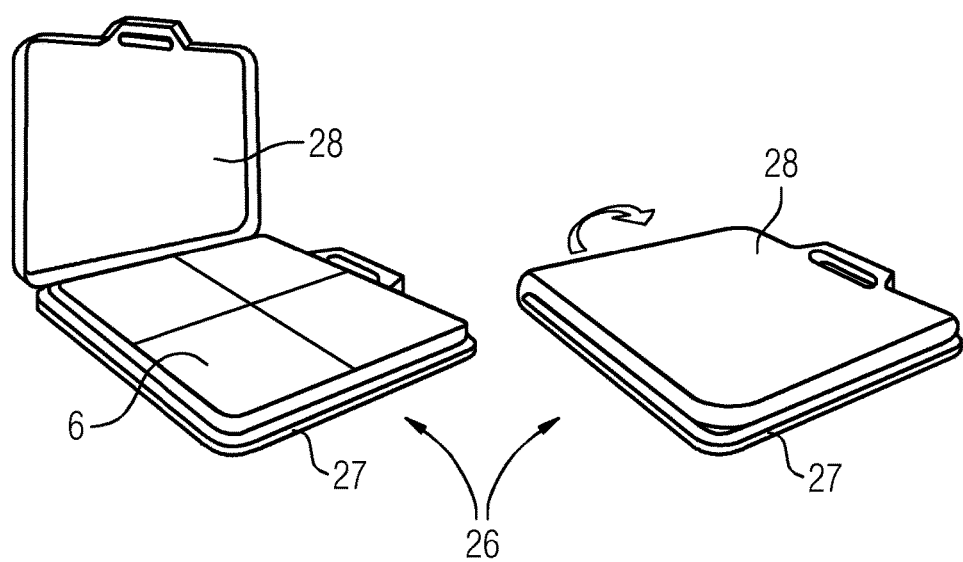
FIG. 5 is a diagrammatic, perspective view of a mobile x-ray detector with a third positioning device.

FIG. 5 depicts a further exemplary embodiment of a positioning device 26. Here, the positioning device 26 is embodied as a case with a base part 27 and a lid part 28 which is fastened to the base part 27 in a swivelable manner. After closing the lid part 28, the flat-panel detector 6 is held in the interior of the positioning device 26 in a defined manner. The components contributing to the functionality of the positioning device 26, such as measuring devices and the like, are integrated into the base part 27 and/or into the lid part 28 in this case.

Although the invention was illustrated more closely and described in detail by the preferred exemplary embodiment, the invention is not restricted to the disclosed examples and other variations can be derived therefrom by a person skilled in the art, without departing from the scope of protection of the invention.

The following is a summary list of reference numerals and the corresponding structure used in the above description of the invention:

1 X-ray device
2 Ceiling mount
3 X-ray tube
4 Patient couch
5 Patient
6 Flat-panel detector
7 Central beam
8 Positioning device
9 U-limb
10 U-limb
11 U-base
12 Accommodation groove
13 Ultrasonic transmitter
14 Microcontroller
15 Battery
16 IR transmitter
17 (unassigned)
18 Positioning aid
19 Ultrasonic receiver
20 IR receiver
21 Control unit
22 Positioning device
23 Arm
24 Latching element
25 (unassigned)
26 Positioning device
27 Base part
28 Lid part

The invention claimed is:

1. A positioning device for a mobile x-ray detector, comprising:
   at least one device selected from the group consisting of at least one marker and at least one sensor for determining a position of the positioning device;
   a number of connection elements for establishing a mechanical connection between the positioning device and the mobile x-ray detector; and
   an arm which is movable from a first position to a second position and back again, said arm having a free end at which at least one of said marker or said sensor is disposed, wherein at least one of said marker or said sensor has a greater distance from the mobile x-ray detector in the second position of said arm than in the first position of the arm.

2. The positioning device according to claim 1, wherein at least one of said marker defines or said sensor determines an orientation of the positioning device.

3. The positioning device according to claim 1, further comprising:
   a computer unit for determining at least one of a position or an orientation of the mobile x-ray detector; and
   an interface for providing at least one of position data or orientation data.

4. The positioning device according to claim 1, wherein said connection elements are embodied to establish at least one of a latching or snap-in connection between the positioning device and the mobile x-ray detector.

5. The positioning device according to claim 1, wherein the positioning device is a frame for at least one of accommodating or holding the mobile x-ray detector.

6. An x-ray device, comprising:
   an x-ray emitter;
   a mobile x-ray detector; and
   a positioning device being connectable to said mobile x-ray detector, said positioning device containing:

at least one device selected from the group consisting of at least one marker and at least one sensor for determining a position of said positioning device;

a number of connection elements for establishing a mechanical connection between said positioning device and said mobile x-ray detector; and an arm which is movable from a first position to a second position and back again, said arm having a free end at which at least one of said marker or said sensor is disposed, wherein at least one of said marker or said sensor has a greater distance from the mobile x-ray detector in the second position of said arm than in the first position of the arm.

7. The x-ray device according to claim 6, further comprising a positioning aid connectable to said x-ray emitter or to a ceiling mount, said positioning aid containing:

at least one further device selected from the group consisting of a further marker and a further sensor for establishing at least one of the position or an orientation of said positioning device for said mobile x-ray detector; and a number of further connection elements for establishing a mechanical connection between said positioning aid and said x-ray emitter or the ceiling mount.

8. A method for mutually aligning a mobile x-ray detector and an x-ray emitter in relation to one another, which comprises the following steps of:

connecting the mobile x-ray detector to a positioning device with an aid of a number of connection elements of the positioning device;

determining a position of the mobile x-ray detector;

providing position data with an aid of the positioning device; and aligning the mobile x-ray detector in relation to the x-ray emitter, and/or vice versa, using the position data.

9. The method according to claim 8, which further comprises:

determining an orientation of the mobile x-ray detector and providing orientation data with an aid of the positioning device; and carrying out an alignment of the mobile x-ray detector in relation to the x-ray emitter, and/or vice versa, using the orientation data.

* * * * *

UNITED STATES PATENT AND TRADEMARK OFFICE
CERTIFICATE OF CORRECTION

PATENT NO.         : 10,111,642 B2
APPLICATION NO.    : 15/183993
DATED              : October 30, 2018
INVENTOR(S)        : Andreas Deinlein et al.

Page 1 of 1

It is certified that error appears in the above-identified patent and that said Letters Patent is hereby corrected as shown below:

On the Title Page

(72) Inventors should read:
Ralf Nanke, Neunkirchen am Brand (DE)

Signed and Sealed this
Fifth Day of February, 2019

Andrei Iancu
*Director of the United States Patent and Trademark Office*